United States Patent
Thorstensson et al.

(10) Patent No.: US 7,608,142 B2
(45) Date of Patent: Oct. 27, 2009

(54) PROCESS FOR THE MANUFACTURE OF A BITUMEN-AGGREGATE MIX SUITABLE FOR ROAD PAVING AND A POLYAMINE COMPOUND AND ITS USE

(75) Inventors: Bengt-Arne Thorstensson, Ytterby (SE); Christos Edengrim, Västerhaninge (SE)

(73) Assignee: Akzo Nobel N.V. (NL)

( * ) Notice: Subject to any disclaimer, the term of this patent is extended or adjusted under 35 U.S.C. 154(b) by 222 days.

(21) Appl. No.: 11/795,002

(22) PCT Filed: Jan. 19, 2005

(86) PCT No.: PCT/EP2005/000564

§ 371 (c)(1),
(2), (4) Date: Sep. 7, 2007

(87) PCT Pub. No.: WO2006/076929

PCT Pub. Date: Jul. 27, 2006

(65) Prior Publication Data

US 2008/0127858 A1    Jun. 5, 2008

(51) Int. Cl.
*C08L 95/00* (2006.01)
*C07C 211/13* (2006.01)
*C09D 195/00* (2006.01)
*B01F 17/16* (2006.01)

(52) U.S. Cl. .................. 106/277; 564/512; 516/43; 516/914

(58) Field of Classification Search .................. 106/277, 106/284.06, 284.4; 564/512; 516/43, 914
See application file for complete search history.

(56) References Cited

U.S. PATENT DOCUMENTS

| | | | |
|---|---|---|---|
| 2,901,461 A * | 8/1959 | Auerbach et al. ............ 564/512 |
| 3,200,155 A * | 8/1965 | Kirkpatrick et al. ......... 564/504 |
| 3,259,512 A | 7/1966 | Dickson et al. |
| 3,324,182 A | 6/1967 | De Brunner et al. |
| 3,418,374 A | 12/1968 | Miller, Jr. et al. |
| 3,518,101 A | 6/1970 | Gzemski et al. |
| 3,615,797 A | 10/1971 | Ohtsuka et al. |
| 3,738,852 A * | 6/1973 | Doi et al. .................... 106/277 |
| 4,017,419 A * | 4/1977 | Ludwig et al. ............... 516/43 |
| 4,172,046 A | 10/1979 | Doi et al. |
| 4,895,600 A * | 1/1990 | Chang et al. ............ 106/284.4 |
| 4,967,008 A | 10/1990 | Friedli et al. |
| 4,985,079 A | 1/1991 | Graf et al. |
| 5,073,297 A | 12/1991 | Schilling |
| 5,928,418 A | 7/1999 | Tamaki et al. |
| 6,013,681 A * | 1/2000 | Asamori et al. ............... 516/43 |
| 6,048,905 A | 4/2000 | Asamori et al. |
| 6,494,944 B1 * | 12/2002 | Wates et al. ................. 106/277 |
| 6,667,382 B1 | 12/2003 | Isobe et al. |
| 6,840,991 B2 * | 1/2005 | Honma et al. ............ 106/284.4 |
| 7,226,501 B2 * | 6/2007 | Thorstensson et al. ...... 106/277 |

OTHER PUBLICATIONS

International Search Report for International Application No. PCT/EP2005/000564, Oct. 19, 2005.

* cited by examiner

*Primary Examiner*—Helene Klemanski
(74) *Attorney, Agent, or Firm*—Ralph J. Mancini

(57) ABSTRACT

According to the invention, a slow setting bitumen-aggregate mix for cold paving is manufactured by a) preparing a cationic oil-in-water emulsion of bitumen in the presence of an emulsifier containing i) a tertiary polyamine selected from the group consisting of a di($C_2$-$C_3$ alkylene)triamine, a tri($C_2$-$C_3$ alkylene)tetraamine, a tetra($C_2$-$C_3$ alkylene)pentaamine, a penta($C_2$-$C_3$ alkylene)hexaamine, a hexa($C_2$ $C_3$ alkylene)heptaamine or a mixture thereof, which amine compounds have only tertiary amine groups and contain one or two aliphatic groups with 8-22 carbon atoms, bound to a nitrogen atom, while the remaining nitrogen substituents are methyl groups and ii) an acid present in such an amount that the aqueous emulsion obtains a pH value from 1-6, preferably 1.5-5, and b) mixing the aqueous emulsion obtained with a solid aggregate. The present invention also comprises a tertiary polyamine selected from said group of tertiary polyamines or a salt thereof with an acid, a process for the production of said tertiary amine, as well as the use of the tertiary polyamine salt as an emulsifying or cohesion increasing agent.

13 Claims, No Drawings

PROCESS FOR THE MANUFACTURE OF A BITUMEN-AGGREGATE MIX SUITABLE FOR ROAD PAVING AND A POLYAMINE COMPOUND AND ITS USE

FIELD OF THE INVENTION

The present invention relates to the manufacture of an aqueous slow-setting bitumen-aggregate mix suitable for cold paving of roads, parking places, sidewalks, and the like. The bitumen-aggregate mix is manufactured by mixing a mineral aggregate, water, and a cationic oil-in-water bitumen emulsion containing a salt between a tertiary polyamine and an acid as an emulsifying and cohesion-increasing agent.

BACKGROUND OF THE INVENTION

It is well-known in the art to prepare cationic oil-in-water emulsions of bitumen and to mix these emulsions with inorganic mineral aggregates. When mineral aggregates and the cationic emulsion are mixed, the emulsion will "break" due to the attraction between the positively charged bitumen droplets and the negatively charged aggregate surfaces. The cationic bitumen droplets will deposit on the aggregate surfaces and be bonded to the aggregates by the electrostatic action at the interface between the bitumen droplets and the aggregates. As emulsifiers, several salts between acids and amine compounds have been suggested. Frequently, acidified amidoamines, imidazolines, fatty polyamines, quaternary ammonium compounds, and mixtures thereof are used. The acid used normally is hydrochloric acid, but also phosphoric acids and other acids containing one or more acid hydrogen atoms have been used.

A variety of polyamines or derivates of polyamines have been used or suggested for use as emulsifiers or anti-stripping agents in bitumen compositions.

Thus, U.S. Pat. No. 3,259,512 discloses a branched polyamine where the branched group contains at least one nitrogen-bonded aminoalkylene group. These polyamines contain at least three primary amino groups and at least one tertiary amino group. The branched polyamines are used as de-emulsifiers for aqueous emulsions or as asphalt additives or as antistripping agents for asphalt-mineral aggregate compositions.

U.S. Pat. No. 3,518,101 describes an aqueous asphalt emulsion which contains, as an emulsifier, a salt between a polybasic acid selected from the group consisting of oxalic acid, tartaric acid, and citric acid, and a diamine compound containing an alkyl group having about 12 to about 22 carbon atoms. The amine groups could be primary, secondary and/or tertiary.

U.S. Pat. No. 3,615,797 discloses a method of making a bitumen with high adhesion properties by adding to the bitumen an ethylene oxide condensate of a long-chain alkyl triamine.

U.S. Pat. No. 4,967,008 discloses polypropylene polyamines which are partially methylated. The compounds are said to have surfactant properties and may, for example, be beneficial as asphalt emulsifiers and antistripping agents.

U.S. Pat. No. 5,073,297 discloses an aqueous bituminous emulsion-aggregate obtained by emulsifying bitumen in water with a particular cationic emulsifier which is a reaction product between modified polyamines and certain polycarboxylic acids and anhydrides. In the preparation of the bituminous emulsion, an acid solution of the emulsifier is used. For instance, hydrochloric, sulphuric, and phosphoric acid or the like can be added until a pH-value below 7 is reached and a clear emulsifier solution is obtained.

U.S. Pat. No. 6,048,905 describes a number of amine compounds suitable as an emulsifier for bitumen. For instance, the amine compounds can be monoamines or polyamines having an aliphatic substituent containing 8-22 carbon atoms. The amines can also be alkoxylated with ethylene oxide and propylene oxide.

When paving, it is today a general practice to prepare a cold mix in a plant and to transport the mix to the work site for paving. Therefore, it is of crucial importance that the mix retains a suitable consistency for paving for at least some hours after mixing. In addition, a strong cohesion between the bitumen and the aggregates as well as between the bitumen and the surface paved is essential. Further, a dense bitumen coating on the aggregates is desired.

SUMMARY OF THE INVENTION

It has now been found that by adding a salt of a specific polyamine it is possible to prepare an aqueous slow-setting bitumen-aggregate mix suitable for cold pavement. The cold mix has an open time of at least two hours and within 24 hours develops a high cohesion between the bitumen and the surface of the aggregates as well as between the bitumen and the paved surface. It also provides a dense bituminous coating of the solid surfaces.

According to the invention, the slow-setting bitumen-aggregate mix for cold paving is manufactured by a) preparing a cationic oil-in-water emulsion of bitumen in the presence of an emulsifier containing i) a tertiary polyamine selected from the group consisting of a di($C_2$-$C_3$ alkylene)triamine, a tri($C_2$-$C_3$ alkylene)tetraamine, a tetra($C_2$-$C_3$ alkylene)pentaamine, a penta($C_2$-$C_3$ alkylene)hexaamine, a hexa($C_2$-$C_3$ alkylene)heptaamine or a mixture thereof, which amine compounds have only tertiary amine groups and one or two substituents containing an aliphatic group of 8-22 carbon atoms, bound to a nitrogen atom, while the remaining substituents are methyl groups, and ii) an acid present in such an amount that the aqueous emulsion obtains a pH value from 1-6, preferably 1.5-5, and b) mixing the aqueous emulsion obtained with a solid aggregate.

The present invention also comprises a tertiary polyamine selected from said group of tertiary polyamines or salts thereof with an acid, a process for the production of said tertiary polyamine, as well as the use of the salt of the tertiary polyamine as an emulsifying or cohesion-increasing agent.

DETAILED DESCRIPTION OF THE INVENTION

The tertiary polyamines of the invention comprise amines which can be linear or branched. The substituents which are not methyl groups suitably are aliphatic groups with 8-22 carbon atoms, preferably aliphatic groups with 10-20 carbon atoms. Further, the aliphatic groups can be straight or branched, saturated or unsaturated. Examples of suitable aliphatic groups are decyl, dodecyl, myristyl, cetyl, stearyl, oleyl, coco alkyl, tallow alkyl, tall alkyl, rapeseed alkyl, linseed alkyl, as well as hydrogenated unsaturated aliphatic groups. The $C_2$-$C_3$ alkylene group is ethylene or a propylene, preferably the group —$(CH_2)_3$—.

Examples of suitable tertiary polyamines are those of the formula

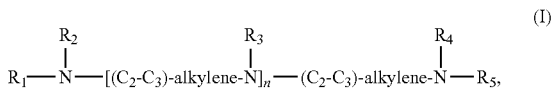

wherein one or two of the groups $R_1$-$R_5$ are an aliphatic group containing 8-22 carbon atoms and the remaining groups of $R_1$, $R_2$, $R_3$, $R_4$, and $R_5$ are methyl, and n is an integer from 1-5.

Another class of tertiary polyamines is formed by those of the formula

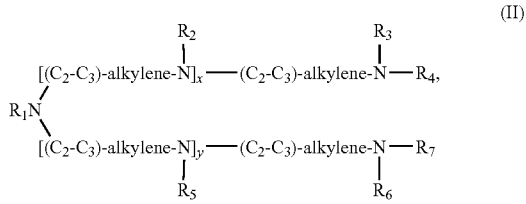

wherein one or two of the groups $R_1$-$R_7$ are an aliphatic group containing 8-22 carbon atoms and the remaining groups of $R_1$-$R_7$ are methyl, and x, y are numbers from 0-4, and the sum of x and y is 0-4.

Still another class of tertiary polyamines is

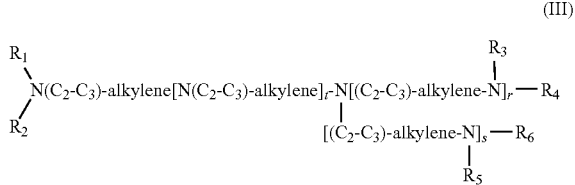

wherein one or two of the groups $R_1$-$R_6$ are an aliphatic group containing 8-22 carbon atoms and the remaining groups of $R_1$-$R_6$ are methyl groups, t is 0-3, r and s are 1-4, and the sum of t, r and s is 2-5.

The acids can be inorganic or organic and monovalent or polyvalent. Examples of organic acids are carboxylic acids, such as acetic acid, oxalic acid, malonic acid, tartaric acids, maleic acid, succinic acid, and citric acid. Other organic acids are alkyl esters of phosphoric acid. Examples of inorganic acids are hydrochloric acid, sulphuric acids, ortophosphoric acid, and phosphorous acid. Especially preferred are polyvalent acids and hydrochloric acid.

The polyamines of the invention can be produced by methylation of the corresponding non-methylated or only partially methylated polyamines. The methylation can be performed with conventional methods, for instance methylation with a methyl halide, such as methyl chloride, methyl bromide or methyl iodide, with dimethyl sulfate or dimethyl carbonate. Another method of methylation of the nitrogen atoms is to perform a reductive amination with formaldehyde in the presence of a reducing agent, such as formic acid or hydrogen. If the reducing agent is hydrogen, the process is performed in the presence of a hydrogenation catalyst containing for example nickel, cobalt, copper or boron or a mixture of two or more of these metals.

Suitable polyamines for methylation are well-known. Thus, suitable polypropylene polyamines can be manufactured by first reacting a primary or secondary amine substituted with one or two aliphatic groups of 8-22 carbon atoms with acrylonitrile, and then performing a hydrogenation step. Thereafter, the nitrilation and hydrogenation steps are repeated until the desired number of nitrogen atoms has been obtained. Polyethylene polyamines suitable for methylation are also known and can be obtained by well-known amination reactions performed in the presence of a dehydrogenation/hydrogenation catalyst. Thus, for instance, a secondary or tertiary monoethanol monoamine with one or two aliphatic substituents of 8-22 carbon atoms or a primary or secondary amine with one or two substituents of 8-22 carbon atoms can, in accordance with well-known principles, be reacted with compounds selected from the group comprising ammonia, monoethanol monoamine, triethanolamine, ethylene diamine, diethylene triamine and/or higher polyethylene polyamines in appropriate amounts.

Polypropylene polyamines suitable for producing the methylated polalkylene polyamines of formula I can be prepared by first reacting a primary or secondary amine substituted with one or two aliphatic groups of 8-22 carbon atoms with equal molar amounts of acrylonitrile and thereafter performing a catalytic hydrogenation. The nitrilation and hydrogenation steps can then be repeated until the desired number of amine groups has been obtained. The corresponding polyethylene polyamines of formula I can be prepared by reacting, in accordance with well-known principles, a primary or secondary amine having one or two aliphatic groups having 8-22 carbon atoms or the corresponding ethanolamines with monoethanolamine, ethylene diamine, diethylene triamine and/or higher polyethylene polyamines in the presence of a conventional dehydrogenation/hydrogenation catalyst at about 150 to 200° C. Finally, any remaining hydroxyl groups are aminated with ammonia.

Suitable non-methylated polypropylene polyamines of formula II can be obtained by starting with a primary amine substituted with an aliphatic group of 8-22 carbon atoms. By reacting the primary amine with acrylonitrile in the presence of an acid as catalyst two moles of acrylonitrile can be added to one mole of the amine in one step. The acid is normally removed, after which the alkylaminonitrile is hydrogenated. The reaction can then be continued by adding between one or two equivalents of acrylonitrile, followed by hydrogenation. By repeating the addition of acrylonitrile and hydrogenation, the desired number of amino groups can be obtained. The corresponding polyethylene polyamines can be obtained by reaction between a tertiary diethanolamine substituted with one aliphatic group of 8-22 carbon atoms and ethylene diamine, diethylene triamine and/or monoethanol monoamine. Any remaining hydroxyl groups are finally aminated with ammonia.

The non-methylated polypropylene polyamines of formula III can be obtained by first reacting one equivalent of acrylonitrile and a primary or secondary amine substituted with one or two aliphatic groups of 8-22 carbon atoms in one or more steps and then hydrogenating the reaction product in one or more steps. In order to create branching, two equivalents of acrylonitrile are added to the intermediate in the presence of an acid as a catalyst, whereupon a hydrogenation takes place. The branched polypropylene polyamine can then be further reacted with acrylonitrile, followed by hydrogenation to obtain the desired number of amine groups. The corresponding polyethylene polyamines of formula III can be prepared for example by reacting triethanolamine and a primary or secondary amine substituted with one or two aliphatic groups of 8-22 carbon atoms in a surplus of triethanolamine in the presence of an amination catalyst. The aminated triethanolamine is recovered from the reaction mixture and then further aminated with ethylene diamine, diethylene triamine and/or monoethanolamine in the presence of hydrogen. Finally, any remaining hydroxyl groups are aminated with ammonia.

The aggregate is an inorganic material which normally contains a densely graded inorganic material, such as blast furnace slag and minerals, e.g. granite, limestone, and dolomite. The particle size distribution suitably includes both fines and coarser particles. A typical aggregate consists of the following fractions:

| | |
|---|---|
| 0-4 mm | 44% |
| 4-8 mm | 23% |
| 8-12 mm | 33% |

Suitable kinds of bitumen for use in the present invention are those commonly used in road paving and in the techniques of cold emulsion mix, slurry seal, microsurfacing, and the like and include but are not limited to those having an AC grade from AC-15 to AC-35. The bitumen used in the present invention also includes petroleum straight asphalt, semiblown asphalt, out-back asphalt, natural asphalt, petroleum tar, pitch, heavy oil, and a mixture of two or more of these products. The bitumen can also be modified with polymers such as SBS and EVA.

An aqueous bitumen-aggregate mix according to the invention normally contains
100 parts by weight of an aggregate,
6-20, preferably 8-15 parts by weight of bitumen,
0.1-3, preferably 0.2-2.5 parts by weight of the salt between the polyamine according to the invention and an acid.

The aqueous bitumen-aggregate mix can be produced by mixing a blend containing the mineral aggregate and 5-35% of water, calculated on the weight of the aggregate, with 10-40% of the aqueous acidic oil-in-water emulsion of the bitumen, calculated on the weight of the aggregate. Said bitumen emulsion normally contains 50-70% by weight of bitumen, 0.4-20, preferably 2-14% by weight of a salt between an acid and the polyamine according to the invention, and 21-43%, preferably 25-40% by weight of water. The total amount of water in the bitumen-aggregate mix normally is between 12 and 25% by weight of the aggregate.

Also other components can be present in the bitumen-aggregate mix and in the bitumen emulsion. Thus, the bitumen emulsion can contain other emulsifiers which are nonionic or cationic surfactants containing at least one hydrocarbon group of 6-22 carbon atoms, preferably 8-22 carbon atoms, such as amide compounds, ethyleneoxy-containing amide compounds, acidified amidoamines, ethyleneoxy-containing amidoamines, imidazolines, polyamines, and quaternary ammonium compounds, and mixtures thereof. Specific examples of other emulsifiers are salts between acids, suitably polyvalent acids, such as a polyvalent phosphoric acid, and an imidazoline compound of the formula

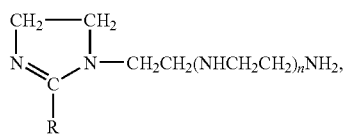

wherein R is an alkyl group of 5-21, preferably 7-19 carbon atoms, and n is a number from 0-3; or an amidoamine compound of the formula

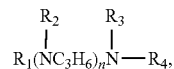

wherein one or two of the groups $R_1$, $R_2$, $R_3$, and $R_4$ are an acyl group of 6-22, preferably 8-20 carbon atoms and the remaining groups $R_1$, $R_2$, $R_3$, and $R_4$ are lower alkyl groups of 1-4 carbon atoms, preferably methyl, hydroxyethyl, hydroxypropyl or hydrogen, and n is a number from 1 to 4, with the proviso that at least one nitrogen atom is part of an amino group.

The bitumen-aggregate mix can also contain an additional organic binder, for example latex, selected from the group consisting of SBR, polychloroprene, and natural latex, and mixtures thereof. The latex can be incorporated into the bitumen emulsion or directly into the mix. It may be necessary to use cationic or nonionic grades of latex compatible with the emulsion, as is well known in the art of emulsion formulation. The latex binder may impart desirable properties to the cured mixture including improved durability. The bitumen aggregate mix can also contain other components such as fibres and pigments.

The invention is further illustrated by the working examples below.

EXAMPLE 1

In a batchwise reactor acrylonitrile and a tallow alkyl amine were reacted at a temperature of 70-100° C. After the reaction, the obtained aminopropionitrile was hydrogenated in the presence of ammonia and a nickel-containing catalyst. The main product obtained was (tallow alkyl)NH(CH$_2$)$_3$NH$_2$, which was then reacted with acrylonitrile and thereafter hydrogenated as described above. The reaction mixture was analyzed by titration of the nitrogen in order to determine the total amount of basic nitrogen and the amounts of tertiary, secondary, and primary nitrogen. The major component was a triamine of the formula (tallow alkyl)NH(CH$_2$)$_3$NH(CH$_2$)$_3$NH$_2$ and its total yield was above 80% by weight.

The primary and secondary nitrogen atoms of the triamine were then methylated by reductive methylation with formaldehyde in the presence of formic acid as the reducing agent. In the process 100 g of the triamine were slowly added at a temperature of 80° C. to an aqueous solution containing 91.5 g of formic acid, 52.3 g of NaOH, and 47.1 g of formaldehyde. After completion of the methylation, the phase containing the methylated triamine was separated from the water by adding an aqueous solution containing 46% by weight of NaOH. The methylation degree of the triamine was controlled by the same method as described above. The yield of the methylated triamine, (tallow alkyl)N(CH$_3$)(CH$_2$)$_3$N(CH$_3$)(CH$_2$)$_3$N(CH$_3$)$_2$, was found to be about 98% by weight of the starting triamine.

EXAMPLE 2

The (tallow alkyl)-dipropylene triamine disclosed in Example 1 was further reacted with one equivalent of acrylonitrile, whereupon the obtained nitrile derivative was hydrogenated. The nitrilation step, the hydrogenation step, and the methylation step were performed according to the same principles as described in Example 1. The major reaction product was a tetraamine of the formula (tallow alkyl)-N(CH$_3$)[(CH$_2$)$_3$N(CH$_3$)]$_2$(CH$_2$)$_3$N(CH$_3$)$_2$, and its structure was confirmed by the analyses described above. The total yield was about 80% by weight.

EXAMPLE 3

Several aqueous bitumen-aggregate mixes were prepared by mixing
a) 8 parts by weight of an aqueous oil-in-water bitumen emulsion containing 5.2 parts by weight of bitumen and an emulsifier in an amount in accordance with Table 1,
b) 100 parts by weight of an aggregate of granite, consisting of the following fractions 0-4 mm 44%, 4-8 mm 23%, 8-12 mm 33%, and
c) 5 parts by weight of water, at a temperature of about 20° C. The bitumen used in the emulsion had an acid value of 4 mg KOH/g of bitumen. The emulsifiers used in the preparation were the following.

| | Emulsifiers |
|---|---|
| Designation | Structure |
| A | Salt between orthophosphoric acid and the methylated triamine described in Example 1 |
| B | Salt between orthophosphonic acid and the methylated tetraamine described in Example 2 |
| C | Salt between orthophosphoric acid and (tallow alkyl)-$N(CH_3)C_3H_6N(CH_3)_2$ |
| D | Salt between orthophosphoric acid and (tallow alkyl)-$NH(C_3H_6NH)_2C_3H_6NH_2$ |
| E | Salt between hydrochloric acid and (tallow alkyl)-$NH(C_3H_6NH)_2C_3H_6NH_2$ |
| F | (Tallow alkyl)$N^+(CH_3)_2C_3H_6N^+(CH_3)_2 + 2Cl$ |

The pH of the emulsions was adjusted with orthophosphoric acid or hydrochloric acid to a pH value of 2. After their preparation, the asphalt mixes were spread out on a surface for six hours at 20° C., whereupon the workability of the asphalt mixes was determined according to the Workability Test of Nynäs Bitumen AB, Identification No. FBMASS2.BGu, dated 950621. According to said test, the workability of an asphalt mix was measured as the force needed to form, in a box, an asphalt layer of 50 mm thickness and 140 mm long by 230 mm broad from 20+ kg of the asphalt mix by shearing off the surplus with an aluminium plate moving 140 mm during 14 s. According to this test, an asphalt mix of good workability should have a value lower than 200 N. The results obtained are also shown in Table 1.

TABLE 1

Compositions of the mixes and their workability

| | Emulsifier | | |
|---|---|---|---|
| Mix No. | Type | Parts by weight | Workability, N |
| 1 | A | 1.0 | 78 |
| 2 | B | 1.0 | 130 |
| 3 | C | 1.0 | 571 |
| 4 | D | 1.0 | 586 |
| 5 | E | 0.6 | 1120 |
| 6 | F | 1.0 | 1248 |

From the results it is evident that the emulsifiers A and B according to the invention impart essentially better workability to the asphalt compositions than the comparison emulsifiers C-F.

The invention claimed is:

1. A process for the manufacture of a slow-setting bitumen-aggregate mix which comprises
a) preparing a cationic oil-in-water emulsion of bitumen in the presence of an emulsifier containing
i) a tertiary polyamine, selected from the group consisting of a di($C_2$-$C_3$ alkylene)triamine, a tri($C_2$-$C_3$ alkylene)tetraamine, a tetra($C_2$-$C_3$ alkylene)pentaamine, a penta($C_2$-$C_3$-alkylene)-hexaamine, and a hexa($C_2$-$C_3$-alkylene)heptaamine or a mixture thereof, which amine compounds have only tertiary amino groups and contain one or two aliphatic groups with 8-22 carbon atoms, bound to the nitrogen atoms, while the remaining nitrogen substituents are methyl groups, and
ii) an acid present in such an amount that the aqueous emulsion obtains a pH value from 1-6, and
b) mixing the aqueous emulsion obtained with a solid aggregate.

2. A process according to claim 1 wherein the tertiary polyamine has the formula

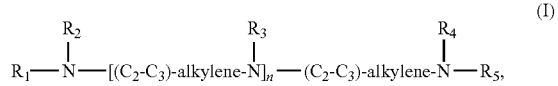

wherein one or two of the groups $R_1$-$R_5$ are an aliphatic group containing 8-22 carbon atoms and the remaining groups of $R_1$-$R_5$ are methyl, and n is an integer from 1-5,

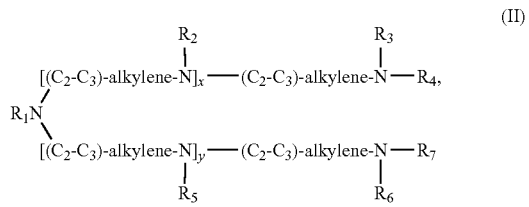

wherein one or two of the groups $R_1$-$R_7$ are an aliphatic group containing 8-22 carbon atoms and the remaining groups of $R_1$-$R_7$ are methyl and x, y is a number from 0-4, the sum of x and y being 0-4, or

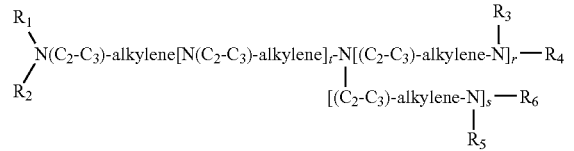

wherein one or two of the groups $R_1$-$R_6$ are an aliphatic group containing 8-22 carbon atoms and the remaining groups of $R_1$-$R_6$ are methyl groups, t is 0-3, r and s are 1-4, and the sum of t, r and s is 2-5, or a mixture thereof.

3. A process according to claim 1 wherein the acid is a polyvalent acid or hydrochloric acid.

4. A process according to claim 1 wherein the $C_2$-$C_3$-alkylene group is the group —$(CH_2)_3$—.

5. A tertiary polyamine selected from the group consisting of a di($C_2$-$C_3$ alkylene)triamine, a tri($C_2$-$C_3$ alkylene)tetraamine, a tetra($C_2$-$C_3$ alkylene)pentaamine, a penta($C_2$-$C_3$ alkylene)hexaamine, a hexa($C_2$-$C_3$ alkylene)heptaamine or a mixture thereof, which amine compounds have only tertiary amine groups and contain one or two aliphatic groups with 8-22 carbon atoms, bound to a nitrogen atom, while the remaining nitrogen substituents are methyl groups, or a salt thereof with an acid.

6. A tertiary polyamine according to claim 5 wherein the polyamine has the formula

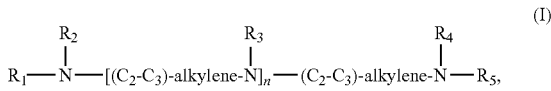

wherein one or two of the groups $R_1$-$R_5$ are an aliphatic group containing 8-22 carbon atoms and the remaining groups of $R_1$-$R_5$ are methyl, and n is an integer from 1-5,

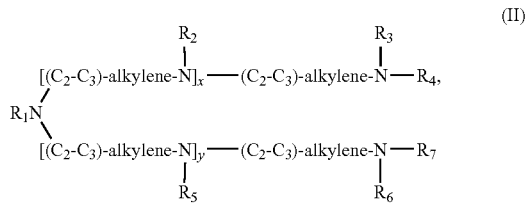

wherein one or two of the groups $R_1$-$R_7$ are an aliphatic group containing 8-22 carbon atoms and the remaining groups of $R_1$-$R_7$ are methyl and x, y is a number from 0-4, the sum of x and y being 0-4, or

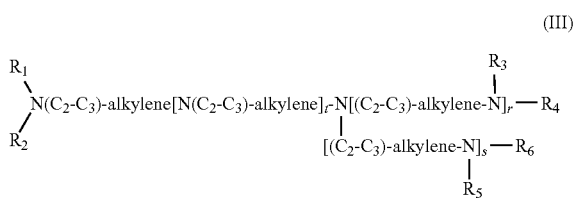

wherein one or two of the groups $R_1$-$R_6$ are an aliphatic group containing 8-22 carbon atoms and the remaining groups of $R_1$-$R_6$ are methyl groups, t is 0-3, r and s are 1-4, and the sum of t, r and s is 2-5, or a mixture thereof.

7. A tertiary polyamine according to claim 6 wherein the $C_2$-$C_3$-alkylene group is the group —$(CH_2)_3$—.

8. An emulsifying and/or cohesion-increasing agent for aqueous bitumen emulsions and/or aqueous bitumen-aggregate mix for paving, said emulsifying and/or cohesion-increasing agent comprising the tertiary polyamine of claim 5.

9. The emulsifying and/or cohesion-increasing agent of claim 8 wherein the acid is a polyvalent acid or hydrochloric acid.

10. A process of producing a tertiary polyamine according to claim 5, said process comprising a step where the corresponding non-methylated polyamine is methylated.

11. A method of emulsifying and/or improving the cohesion of aqueous bitumen emulsions and/or aqueous bitumen-aggregate mix, said method comprising adding to said aqueous bitumen emulsions and/or aqueous bitumen-aggregate from about 0.4 to about 20% by weight of the tertiary polyamine of claim 5, based on the total weight of the emulsion/mix.

12. The method of claim 11 wherein said tertiary polyamine has the formula

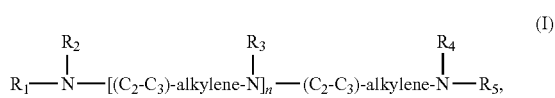

wherein one or two of the groups $R_1$-$R_5$ are an aliphatic group containing 8-22 carbon atoms and the remaining groups of $R_1$-$R_5$ are methyl, and n is an integer from 1-5,

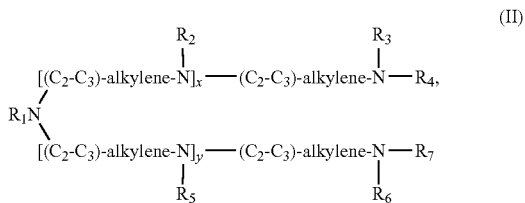

wherein one or two of the groups $R_1$-$R_7$ are an aliphatic group containing 8-22 carbon atoms and the remaining groups of $R_1$-$R_7$ are methyl and x, y is a number from 0-4, the sum of x and y being 0-4, or

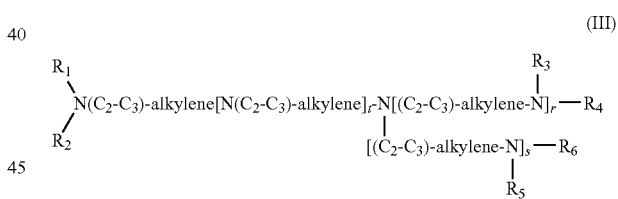

wherein one or two of the groups $R_1$-$R_6$ are an aliphatic group containing 8-22 carbon atoms and the remaining groups of $R_1$-$R_6$ are methyl groups, t is 0-3, r and s are 1-4, and the sum of t, r and s is 2-5, or a mixture thereof.

13. The method of claim 12 wherein in said tertiary polyamine the $C_2$-$C_3$-alkylene group is the group —$(CH_2)_3$—.

* * * * *